United States Patent [19]

Mark

[11] Patent Number: 4,599,463
[45] Date of Patent: Jul. 8, 1986

[54] PROCESS FOR THE PREPARATION OF BISPHENOLS

[75] Inventor: Victor Mark, Evansville, Ind.

[73] Assignee: General Electric Company, Mt. Vernon, Ind.

[21] Appl. No.: 685,904

[22] Filed: Dec. 24, 1984

[51] Int. Cl.$^4$ .............................................. C07C 39/16
[52] U.S. Cl. ...................................... 568/723; 568/722
[58] Field of Search ................................. 568/722, 723

[56] References Cited

U.S. PATENT DOCUMENTS

| | | | |
|---|---|---|---|
| 4,073,815 | 2/1978 | Cornforth et al. | 568/723 |
| 4,460,798 | 7/1984 | Klopfer et al. | 568/723 |

FOREIGN PATENT DOCUMENTS

| | | | |
|---|---|---|---|
| 586890 | 11/1959 | Canada | 568/723 |
| 1543256 | 9/1969 | Fed. Rep. of Germany | 568/723 |
| 794476 | 5/1958 | United Kingdom . | |
| 974982 | 11/1964 | United Kingdom | 568/723 |
| 1216129 | 12/1970 | United Kingdom | 568/723 |

*Primary Examiner*—Werren B. Lone
*Attorney, Agent, or Firm*—John Schneller; Martin B. Barancik

[57] ABSTRACT

Processes for the preparation of bisphenols from phenols and substituted vicinal glycols, or unsaturated alcohols or substituted dienes resulting in bisphenols represented by the general formula:

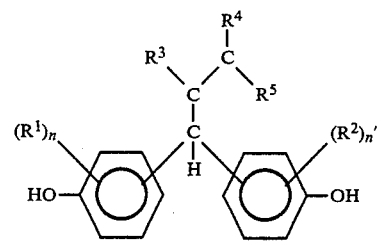

wherein:

$R^1$ and $R^2$ are independently selected from monovalent hydrocarbon and monovalent hydrocarbonoxy radicals of one to four carbon atoms, or from halogen radicals;

$R^3$, $R^4$ and $R^5$ is each a lower alkyl radical, preferably of one to four carbon atoms, aryl radicals, alkaryl radicals, aralkyl radicals, and cycloalkyl radicals, and is the same or different; $R^5$ may also be hydrogen.

n and n$^1$ are independently selected from whole numbers having a value of from 0 to 4 inclusive.

21 Claims, No Drawings

PROCESS FOR THE PREPARATION OF BISPHENOLS

FIELD OF THE INVENTION

The invention relates to a process for the preparation of bisphenols that are suitable for the preparation of polyesters, such as polycarbonates, copolycarbonates, copolyestercarbonates, polyarylates, aliphatic polyesters, polyurethanes, polyepoxides and other polymer systems prepared from bisphenols.

BACKGROUND OF THE INVENTION

Polycarbonates are well-known, commercially available materials which have achieved wide acceptance in the plastics industry. Generally speaking, such polymers exhibit excellent properties of toughness, flexibility, tensile strength, dimensional stability and impact strength surpassing that of many other thermoplastic materials.

Such polymers are prepared by reacting a carbonate precursor, such as phosgene, for example, with a dihydric phenol, such as 2,2-bis(4-hydroxyphenyl)propane, herein refered to as "bisphenol-A," to provide a linear polymer consisting of dihydric phenol units bonded to one another through carbonate linkages.

The dihydric phenols, in turn, are prepared by the reaction of a phenol with a carbonyl compound, usually ketone or aldehyde, and usually in the presence of acids.

SUMMARY OF THE INVENTION

In accordance with the present invention, there are provided novel processes for the preparation of bisphenols from phenols and substituted vicinal glycols, or unsaturated alcohols or substituted dienes resulting in the formation of bisphenols represented by the general formula

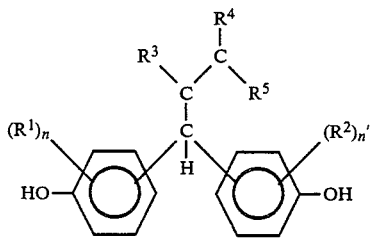

wherein:
$R^1$ and $R^2$ are independently selected from monovalent hydrocarbon and monovalent hydrocarbonoxy radicals of one to four carbon atoms, or from halogen radicals;
$R^3$, $R^4$ and $R^5$ is each a lower alkyl radical, preferably of one to four carbon atoms, aryl radicals, alkaryl radicals, aralkyl radicals, and cycloalkyl radicals, and is the same or different; $R^5$ may also be hydrogen.
n and $n^1$ are independently selected from whole numbers having a value of from 0 to 4 inclusive.

DESCRIPTION OF THE INVENTION

In accordance with the present invention there are provided novel processes for the preparation of bisphenols by the reaction of a phenol of the general formulae

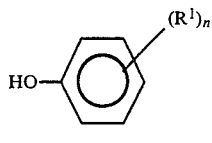

and

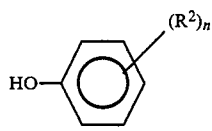

with a difunctional agent of the group
1. a vicinal glycol of the formula

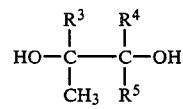

2. an unsaturated alcohol of the formula

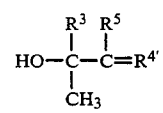

3. a diene of the formulae

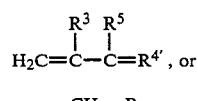

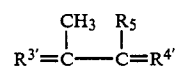

where $R^1$, $R^2$, $R^3$, $R^4$, $R^5$, n and $n'$ are as defined hereinafore, $R^{3'}$ and $R^{4'}$ is each a lower alkylidene radical preferably of one to four carbon atoms aralkylidene and cycloalkylidene radicals under the influence of acid catalysis. The structure of the resultant bisphenols is represented by the general formula

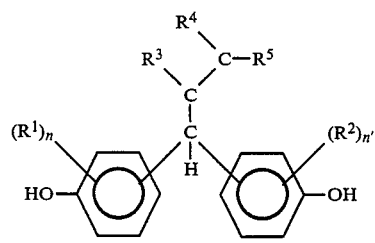

where $R^1$, $R^3$, $R^3$, $R^4$, $R^5$, n and $n'$ are as defined above.

While it is known that in the presence of acids certain vicinal glycols, sometimes referred to as pinacols, do rearrange to a corresponding carbonyl compound, also referred to as a pinacolone, and the rearrangement is the well-known, classic pinacol-pinacolone rearrangement, the resultant bisphenols are not derivable, hence do not derive, from the reaction of the pinacolone with phenols. For instance, the prototype of the rearrangement is that of pinacol itself (2,3-dimethyl-2,3-butanediol), which forms pinacolone(3,3-dimethyl-2-butanone), as shown by the following equation:

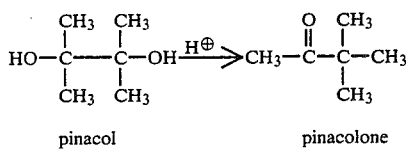

Pinacolone itself, possessing a carbonyl function, could yield in the presence of acids and phenol a bisphenol of the following structure:

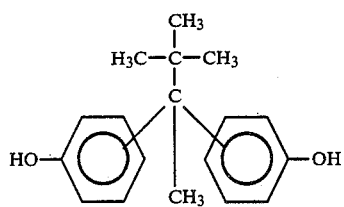

which is, however, not the bisphenol obtained in the present invention, which thus is truly surprising and novel. Instead, the bisphenol formed is the one corresponding to general formula VII, that is:

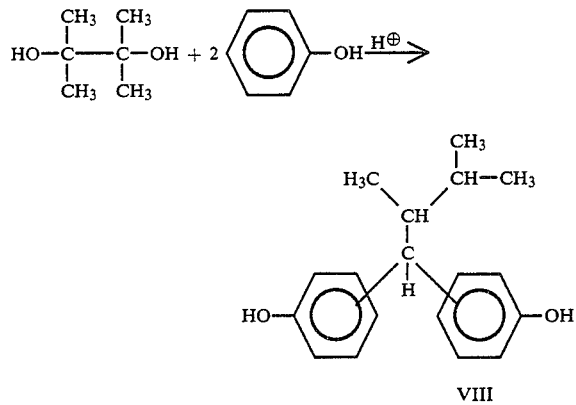

consisting of the 4,4'- (or p, p'-) isomer, which is major, and some of the 2,4'- (or o,p'-) and very little of the 2,2'- (or o,o'-) isomers.

The mechanism of the pinacol-pinacolone rearrangement is discussed in most textbooks of organic chemistry, such as, for example, in "Basic Principles of Organic Chemistry, 2d edition" by J. D. Roberts and M. C. Caserio: W. A. Benjamin, Inc., 1977, New York, N.Y., p. 720; or "Mechanism and Structure in Organic Chemistry" by E. S. Gould: Holt, Rinehart and Winston, 1959, New York, N.Y., pp. 601–610.

Structure proof of bisphenol VIII was accomplished by isolating the pure p,p'-bisphenol, VIII A, as shown in the examples

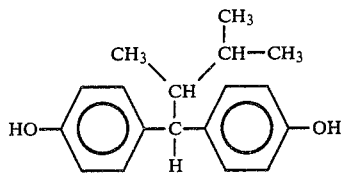

and determining its physical constants and spectral characteristics. While the mass spectrum confirmed the molecular weight, $^1$H and $^{13}$C nuclear magnetic resonance established the structure of the aliphatic moiety and the 4,4'-substitution pattern. To further confirm structure VIII A, phenol was reacted with 2,3-dimethylbutyraldehyde, as shown in Comparative Example 4, below, and the isolated 4,4'-isomer of the resultant bisphenol was found to be identical with the reaction product of pinacol and phenol, by a complete match of its physical and spectral parameters.

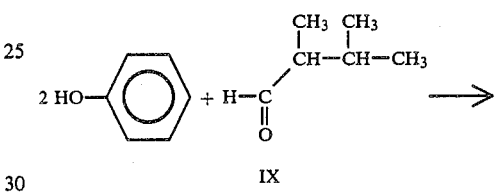

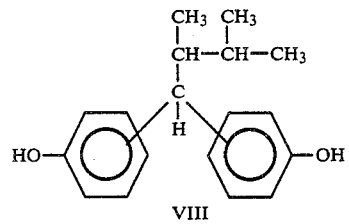

While bisphenols of the general formula VIII are accessible by the condensation process involving the specific precursor aldehydes, no aldehydes of suitable structure, such as IX, are readily available or manufactured commercially. Although they can be synthesized by classical methods by the oxidation of the corresponding alcohols or reduction of the acids, the aldehyde precursors themselves are not readily available.

In contrast, several of the vicinal glycols used in the present invention are commercially available or are readily accessible. The usually symmetrical pinacols are readily available by the reductive coupling of ketones, electrolytically or by various amalgams (sodium, magnesium or aluminium).

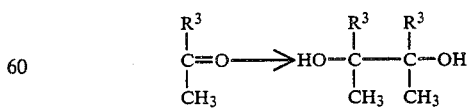

Examples of diols represented by general formula III, in addition to pinacol itself, are 2,3-dimethyl-2,3-pentanediol, 2,3-dimethyl-2,3-hexanediol, 2,3-diphenyl-2,3-butanediol, 2-methyl-3-phenyl-2,3-butanediol, 2-methyl-3-ethyl-2,3-hexanediol, 2-metyl-2,3-butanediol, 3- methyl-2,3-pentanediol, 2,3-di(p-tolyl)-2,3-butanediol, and the like.

Suitable starting materials for the construction of the aliphatic moiety of bisphenols VIII are also dienes V and VI, which react with phenols and acids to yield bisphenols VII:

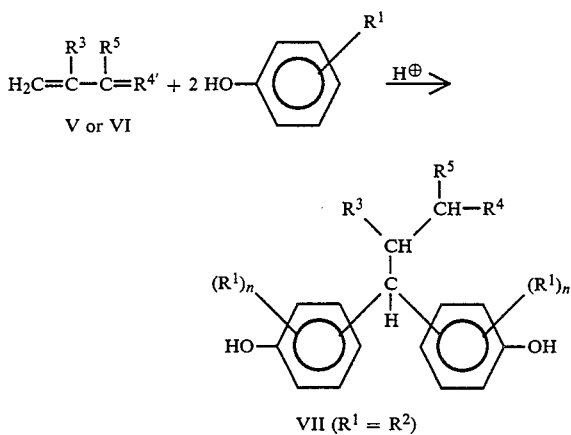

VII ($R^1 = R^2$)

Examples of dienes V and VI are: 2,3-dimethyl-1,3-butadiene, isoprene, 2,3-dimethyl-1,3-pentadiene, 2-methyl-3-phenyl-1,3-butadiene, 2-methyl-1,3-hexadiene, 2-phenyl-1,3-pentadiene. Like the glycols, many of dienes V or VI are commercially available.

Yet a third route to bisphenols VII consists in the reaction of allylically unsaturated alcohols represented by the general formulae IV A, IV B and IV C:

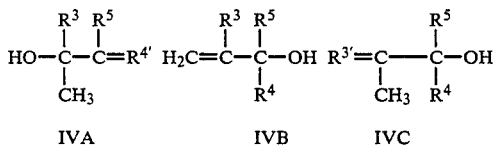

all of which react with electrophilically substitutable phenols to form bisphenols represented by the general formula VII.

Examples of the suitable allylic alcohols are: 2-hydroxy-2-methyl-3-butane, 2,3-dimethyl-3-hydroxy-1-pentene, 2-hydroxy-3-methyl-2-phenyl-3-butane, 3-hydroxy-2,3,4-trimethyl-4-pentene, and the like, some of which are commercially available.

Suitable phenols that form bisphenols of the general formula VII are those that have at least one replaceable hydrogen on the aromatic ring, i.e., where n for $R^1$ or $R^2$ is not more than four.

The preferred halogen radicals represented by $R^1$ and $R^2$ are chlorine and bromine.

The monovalent hydrocarbon radicals represented by $R^1$ and $R^2$ are selected from alkyl radicals, aryl radicals, alkaryl radicals, aralkyl radicals, and cycloalkyl radicals. The preferred alkyl radicals represented by $R^1$ and $R^2$ are those containing from 1 to about 6 carbon atoms. These preferred alkyl radicals include the straight chain and the branched alkyl radicals. Some non-limiting illustrative examples of these preferred alkyl radicals include methyl, ethyl, propyl, isopropyl, butyl, isobutyl, tertiary-butyl, and the like. The preferred aryl radicals represented by $R^1$ and $R^2$ are those containing from 6 to 12 carbon atoms and include phenyl, naphthyl and biphenyl. The preferred alkaryl and aralkyl radicals represented by $R^1$ and $R^2$ are those containing from 7 to about 14 carbon atoms and include benzyl, tolyl, ethylphenyl, and the like. The preferred cycloalkyl radicals represented by $R^1$ and $R^2$ are those containing from 3 to about 8 ring carbon atoms and include cyclopropyl, cyclopentyl, cyclohexyl, and the like.

The monovalent hydrocarbonoxy radicals represented by $R^1$ and $R^2$ are preferably selected from alkoxy radicals and aryloxy radicals. The preferred alkoxy radicals are those containing from 1 to about 6 carbon atoms. The preferred aryloxy radical is the phenoxy radical.

In the dihydric phenols of Formula VII when more than one $R^1$ substituent is present, i.e., when n is equal to from 2 to 4, they may be the same or different. The same is true for the $R^2$ substituent. If n or n' is zero, then the ring carbon atoms of the aromatic nuclear residue are substituted with hydrogen atoms.

The monovalent hydrocarbon radicals represented by $R^3$, $R^4$ and $R^5$ are selected from alkyl radicals, cycloalkyl radicals, aryl radicals, alkaryl radicals, and aralkyl radicals.

The preferred alkyl radicals represented by $R^3$, $R^4$ and $R^5$ are those containing from 1 to about 8 carbon atoms. These alkyl radicals include the branched alkyl radicals and the straight chain alkyl radicals. Some illustrative non-limiting examples of these preferred alkyl radicals include methyl, ethyl, propyl, butyl, isobutyl, tertiary-butyl, pentyl, neopentyl, and the like.

The preferred aryl radicals represented by $R^3$, $R^4$ and $R^5$ are those containing from 6 to 12 carbon atoms, i.e., phenyl, naphthyl and biphenyl. The preferred alkaryl and aralkyl radicals are those containing from 7 to about 14 carbon atoms, e.g., benzyl, tolyl, ethylphenyl, etc.

The preferred cycloalkyl radicals represented by $R^3$, $R^4$ and $R^5$ are those containing from 4 to about 8 ring carbon atoms. Some illustrative non-limiting examples of these preferred cycloalkyl radicals include cyclobutyl, cyclopentyl, cyclohexyl, and the like.

The divalent hydrocarbon radicals represented by $R^{3'}$ and $R^{4'}$ are selected fro alkylidene radicals, aralkylidene radicals and cycloalkylidene radicals.

The preferred alkylidene radicals represented by $R^{3'}$ and $R^{4'}$ are those containing from 1 to about 8 carbon atoms. Some illustrative non-limiting examples of these preferred alkylidene radicals include methylene, ethylidene, propylidene, ispropylidene, neopentylidene and the like.

The preferred cycloalkylidene radicals represented by $R^{3'}$ and $R^{4'}$ are those containing from 4 to 8 ring carbon atoms. Some illustrative non-limiting examples of these cycloalkylidene radicals include cyclobyutylidene, cyclopentylidene, cyclohexylidene and cyclooctylidene.

In order to obtain the dihydric phenols of Formula VII, one mole of the reactants of Formulae III, IV, V and VI is reacted with two moles of a phenol of Formula I or II, or with one mole of a phenol of Formula I and one mole of a phenol of Formula II in the presence of an acid catalyst. Some illustrative non-limiting examples of suitable acid catalysts that may be employed include hydrochloric acid, hydrobromic acid, poly(styrene sulfonic acid), sulfuric acid, benzene sulfonic acid, and the like. The phenols of Formulae I and II are reacted with the glycol, diene or allylic alcohol of Formulae III, IV, V and VI in the presence of said acid catalyst, such that coreaction between said phenols and said reactants will occur to form the dihydric phenol of Formula VII. The reaction, generally, proceeds satisfactorily at about one atmosphere of pressure and at temperatures of from about 0° to room temperature to about 100° C.

The amount of the acid catalyst employed is a catalytic amount. By catalytic amount is meant an amount effective to catalyze the reaction between the aldehyde and the phenol. Generally this amount is in the range of from about 0.1 to about 10%. However, in actual practice it is usually somewhat higher since the water coproduct formed in the reaction dilutes the acid catalyst and makes it somewhat less effective (slowing the reaction) than in its undiluted state.

The phenols of Formulae I and II may, of course, be the same. In that case, one mole of the reactants of Formulae III, IV, V and VI is reacted with two moles of the phenol.

Some non-limiting illustrative examples of the dihydric phenols represented by Formula VII include:

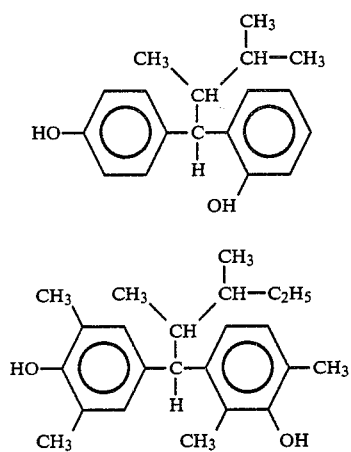

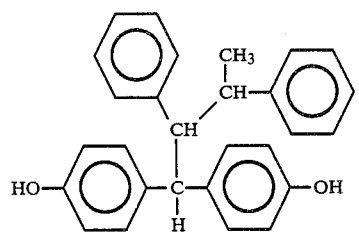

-continued

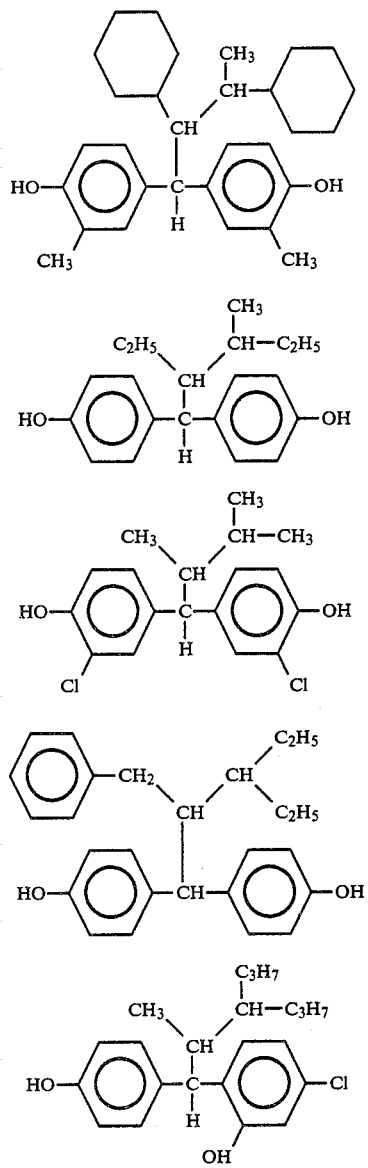

These bisphenols are suitable for the preparation of polycarbonates, copolycarbonates, copolyestercarbonates, polyesters, including polyarylates, polyurethanes, polyepoxides and other polymer systems prepared from bisphenols.

The novel carbonate polymers of the invention contain repeating structural units represented by the general formula

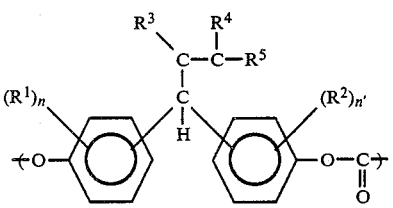

wherein $R^1$, $R^2$, $R^3$, $R^4$, $R^5$, n and n' are as defined above.

The carbonate precursor may be a carbonyl halide, a diarylcarbonate, or a bishaloformate. The preferred carbonate precusors are the carbonyl halides. The preferred carbonyl halides include carbonyl chloride, carbonyl bromide, and mixtures thereof. The preferred carbonyl halide is carbonyl chloride, also known as phosgene.

These high molecular weight aromatic carbonate polymers generally have an average molecular weight in the range of from about 10,000 to about 150,000, preferably from about 20,000 to about 100,000.

One method of preparing the high molecular weight aromatic carbonate polymers of the present invention involves the heterogeneous interfacial polymerization system utilizing an aqueous caustic solution, an organic water immiscible solvent such as methylene chloride, at least one dihydric phenol selected from phenols represented by Formulae I and II, a carbonate precursor such as phosgene, a catalyst, and a molecular weight regulator.

The catalysts which are employed herein can be any of the suitable catalysts that aid the polymerization of a dihydric phenol with phosgene. Suitable catalysts include, but are not limited to, tertiary amines such as triethylamine, quaternary ammonium compounds, and quaternary phosphonium compounds.

Another useful method for preparing the carbonate polymers of the present invention involves the use of an organic solvent system wherein the organic solvent system may also function as an acid acceptor, at least one dihydric phenol of Formula I and/or II, a molecular weight regulator, and a carbonate precursor such as phosgene.

The molecular weight regulators employed may be any of the known compounds which regulate the molecular weight of the carbonate polymer by a chain terminating mechanism. These compounds include, but are not limited to, phenol, tertiary butyl phenol, and the like.

The temperature at which phosgenation reaction proceeds may vary from below 0° C. to above 100° C. The reaction proceeds satisfactorily at temperatures from room temperature, about 25° C. to 50° C. Since the reaction is exothermic, the rate of phosgene addition or a low boiling solvent such as methylene chloride, or just plain external cooling, may be used to control the reaction temperature.

The carbonate polymers of the present invention may optionaly have admixed therewith certain commonly known and used additives such as antioxidants; antistatic agents; fillers such as glass fibers, mica, talc, clay, and the like; impact modifiers; ultraviolet radiation absorbers such as the benzophenones and the benzotriazoles; plasticizers; hydrolytic stabilizers such as the epoxides disclosed in U.S. Pat. Nos. 3,489,716; 4,138,379 and 3,839,247, all of which are incorporated herein by reference; color stabilizers such as the organophosphites disclosed in U.S. Pat. Nos. 3,305,520 and 4,118,370, both of which are incorporated herein by reference, and flame retardants.

Some particularly useful flame retardants are the alkali and alkaline earth metal salts of sulfonic acids. These types of flame retardants are disclosed in U.S. Pat. Nos. 3,933,734; 3,948,851; 3,926,908; 3,919,167; 3,909,490; 3,953,396; 3,931,100; 3,978,024; 3,953,399; 3,917,559; 3,951,910 and 3,940,366, all of which are incorporated herein by reference.

Another embodiment of the present invention is a carbonate copolymer obtained by reacting, as essential components, (i) a carbonate precursor, (ii) at least one dihydric phenol selected from the dihydric phenols represented by Formula VII, and (iii) at least one dihydric phenol represented by the general formula

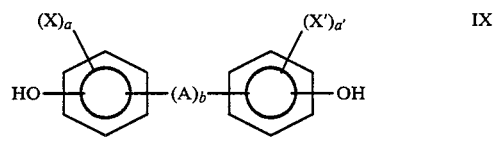
IX wherein A represents an alkylene radical, a cycloalkylene radical, an alkylidene radical, a cycloalkylidene radical,

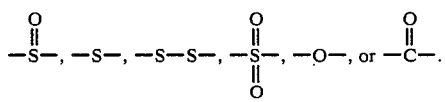

The dihydric phenols of Formula IX are well known and are generally used in making conventional polycarbonates.

In Formula IX each X' and X is independently selected from halogen radicals, such as chlorine and bromine; monovalent hydrocarbon radicals; and monovalent hydrocarbonoxy radicals. The monovalent hydrocarbon radicals are selected from alkyl radicals, preferably those containing from 1 to about 6 carbon atoms; aryl radicals, preferably those containing from 6 to 12 carbon atoms, such as phenyl, naphthyl and biphenyl; alkaryl radicals and aralkyl radicals, preferably those containing from 7 to about 14 carbon atoms; and cycloalkyl radicals, preferably those containing from 4 to about 8 ring carbon atoms.

The monovalent hydrocarbonoxy radicals represented by X and X' are preferably selected from alkoxy radicals and aryloxy radicals. The letters a and a' independently represent whole numbers having a value of from 0 to 4, inclusive. The letter b is either zero or one.

The alkylene radicals represented by A are those containing from 2 to about 6 carbon atoms. The alkylidene radicals represented by A are those containing from 1 to about 6 carbon atoms. The cyclalkylene and cycloalkylidene radicals represented by A are those containing from 4 to about 7 ring carbon atoms. The alkylene and alkylidene radicals represented by A are straight chain alkylene and alkylidene radicals.

In the dihydric phenol compounds represented by Formula IX when more than one X substituent is present, they may be the same or different. The same is true for the X' substituents. Where b is zero in Formula IX, the aromatic rings are directly joined with no intervening alkylene or other bridge. The positions of the hydroxyl groups and X or X' on the aromatic nuclear residues can be varied in the ortho, meta or para positions, and the groupings can be in a vicinal, asymmetrical or symmetrical relationship, where two or more ring carbon atoms of the aromatic hydrocarbon residue are substituted with X or X' and hydroxyl groups.

Some non-limiting illustrative examples of suitable dihydric phenols represented by Formula IX include:
1,1-bis(4-hydroxyphenyl)cyclohexane;
2,2-bis(4-hydroxyphenyl)propane(bisphenol-A);
3,3-bis(3-methyl-4-hydroxyphenyl)pentane;
1,1-bis(3-methyl-4-hydroxyphenyl)ethane;
2,2-bis(3,5-dibromo-4-hydroxyphenyl)propane;
3,3'-dichloro-4,4'-dihydroxydiphenyl;
bis(3-chloro-4-hydroxyphenyl)sulfone;
3,3'-diethyl-4,4'-dihydroxydiphenyl;
bis(4-hydroxyphenyl)sulfide; and the like.

The carbonate copolymers obtained by reacting (i) a carbonate precursor, (ii) at least one dihydric phenol selected from dihydric phenols represented by Formula VII, and (iii) at least one dihydric phenol represented by Formula IX will contain the following repeating structural units:

VIII; and

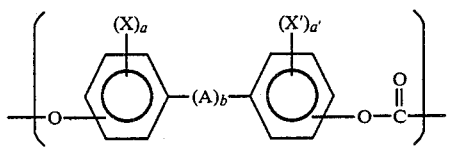

X.

wherein X, X', a, a', A and b are as defined hereinafore.

The procedures for producing the carbonate copolymers are generally similar to those described hereinafore for producing the polymers of the instant invention. The carbonate copolymers may likewise have admixed therewith the various additives described supra.

Yet another embodiment of the present invention is a polycarbonate resin blend comprised of (i) at least one polycarbonate resin of the present invention (hereinafter referred to as resin A); and (ii) at least one polycarbonate resin derived from (a) a carbonate precursor, and (b) at least one dihydric phenol of Formula IX (hereinafter referred to as resin B). These blends may generally contain from about 10 to about 90 weight percent of resin A, based on the total amount of resins A and B present in the blends. The present blends are prepared by first preforming the various resins and thereafter physically mixing or blending these resins together. These blends may optionally contain the various additives described supra.

DESCRIPTION OF THE PREFERRED EMBODIMENT

The following examples are set forth in order to more fully and clearly illustrate the present invention. It is intended that the examples be considered as illustrative rather than limiting the invention as disclosed and claimed herein. In the examples, all parts and percents are on a weight basis unless otherwise indicated.

The following examples illustrate the preparation of the novel dihydric phenols of the present invention.

EXAMPLE 1

This example illustrates the preparation of 2,3-dimethyl-butylidene bisphenol (dihydric phenol represented by Formula VIII) from pinacol.

Into a warm solution of 39.4 g (0.3 mole) of 2,3-dimethyl-2,3-butanediol (pinacol) in 282 g. (3.0 mole) of molten phenol there was introduced gaseous hydrogen chloride at a rate of ca. 1 bubble per second while maintaining the reaction temperature at near 50° C. At about every hour a small sample was taken for gas chromatographic analysis, which indicated the gradual formation of products in the bisphenol range. After about 5 hours, after the concentration of the bisphenols reached its peak, the excess phenol was removed by distillation in water aspirator vacuum and the residue, which solidified on cooling, was slurried with methylene chloride and filtered. The slightly off-white crystals, which had a melting point of 165.5° to 167° C., were identified as the p,p'-isomer of the title compound by carbon and proton nuclear magnetic resonance, gas chromatography, and infrared spectroscopy. The methylene chloride wash contained, in addition to some of the p,p'-, also the o,p'- and some o,o'-isomers.

EXAMPLE 2

This example illustrates the preparation of 4,4'-(2,3-dimethylbutylidene)bisphenol from phenol and 2,3-dimethylbutadiene.

The procedure of Example 1 was repeated, except that instead of hydrogen chloride, 65 g. of an acidic ion-exchange resin (Amberlyst 15) was used as the catalyst at the temperature range of from 40° to 55° C. After about 7 hours the catalyst was filtered off and the phenol solution was worked-up as in Example 1, yielding the title compound as residue.

EXAMPLE 3

Preparation of 4,4'-(2,3-dimethylbutylidene)bisphenol from phenol and the commercially available 2,3-dimethyl-3-buten-2-ol.

Repeating the procedure of Example 1 with 30.0 g. (0.3 mole) of 2,3-dimethyl-3-buten-2-ol, instead of pinacol, yielded with phenol and hydrogen chloride the title compound of melting point 165.5°-167° C.

COMPARATIVE EXAMPLE 4

This example illustrates the preparation 4,4'-(2,3-dimethylbutylidene)bisphenol by conventional means from 2,3-dimethylbutyraldehyde and phenols, and it is outside the scope of the present invention.

The commercially available 2,3-dimethyl-1-butanol was oxidized to the commercially not available 2,3-dimethyl-butyraldehyde by adding, at ambient temperature, to a solution of 7.1 g. (0.07 mole) of the alcohol in 100 ml. of methylene chloride a solution of 23.7 g. (0.11 mole) of pyridinium chlorochromate in 200 ml. of methylene chloride, in the course of one hour, during which the temperature rose from 20° to 31° C. After stirring at ambient temperature for another hour, the solution was decanted from the black sludge, washed twice with 150 ml., each, of concentrated hydrochloric acid and the somewhat hazy solution with a green cast was passed through a 15 cm. high bed of Florisil. After distilling off methylene chloride, the aldehyde distilled over between 102° and 111° C. and was found to be 94% pure by gas chromatography.

The preparation of the bisphenol was carried out by saturating with hydrogen chloride a solution of 5.0 g. (0.05 mole) of the aldehyde in 47 g. (0.5 mole) of warm phenol, stirring the reaction mixture for 1 hour at between 45° and 52° C. and stripping off the acid and excess phenol mixture in aspirator vacuum. Trituration of the solid distillation residues left behind pale yellow crystals that were identified as 4,4'-(2,3-dimethylbutylidene)bisphenol by carbon and proton nuclear magnetic resonance, infrared spectroscopy, and gas chromatography and whose melting point was 164° to 167° C., undepressed when mixed with the crystals of the bisphenol prepared in Example 1.

EXAMPLE 5

This example illustrates the preparation of bisphenols from pinacol and an alkyl substituted phenol.

The procedure of Example 1 was repeated by using 11.8 g. (0.1 mole) of 2,3-dimethyl-2,3-butanediol and 122 g. (1.0 mole) of 2,6-xylenol(2,6-dimethylphenol), except that the solid residue obtained after the distillation of the xylenol was recrystallized twice from cyclohexane. The resultant white crystals had a melting point of 153° to 154.5° C. and were found to be 100% pure by gas chromatography. Carbon and proton nuclear magnetic resonance spectroscopy confirmed their structure as 2,2',6,6'-tetramethyl-4,4'-(2,3-dimethylbutylidene)-bisphenol.

COMPARATIVE EXAMPLE 6

This example describes the preparation of the bisphenol by conventional means from 2,6-xylenol and 2,3-dimethylbutyraldehyde and is outside the scope of the present invention.

The procedure of Example 4 was repeated by using 11.8 g. (0.118 mole) of 2,3-dimethylbutyraldehyde (obtained as described in Example 4) and 122 g. (1.0 mole) of 2,6-xylenol. The structure of the resultant bisphenol was found identical with that of Example 5.

EXAMPLE 7

This example illustrates the preparation of a bisphenol from a diene and a disubstituted phenol.

The procedure of Example 2 was repeated, except that 10.3 g. (0.125 mole) of 2,3-dimethyl-1,3-butadiene, 152.8 g (1.25 mole) of 2,6-xylenol, and 50 g. Amberlyst 15 ion exchange resin catalyzed was utilized. The reduction product was found to be identical with those of Examples 5 and 6.

What is claimed is:

1. A process for the preparation of a bisphenol of the formula (I)

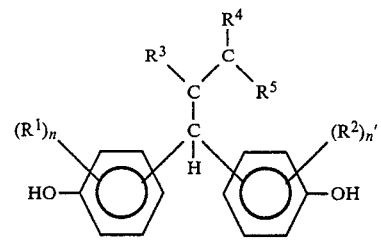

wherein:

$R^1$ and $R^2$ are independently selected from monovalent hydrocarbon and monovalent hydrocarbonoxy radicals of one to four carbon atoms, or from halogen radicals; and $R^3$, $R^4$ and $R^5$ are independently selected from a lower alkyl radical of one to eight carbon atoms, an aryl radical of six to twelve carbon atoms, an alkaryl radical of seven to fourteen carbon atoms, an aralkyl radical of seven to fourteen carbon atoms and a cycloalkyl radical of from three to eight ring carbon atoms, and $R^5$ may also be hydrogen;

n and n' are independently selected from whole numbers having a value of from 0 to 4 inclusive, comprising:

a step of reacting a phenol selected from the group consisting of:

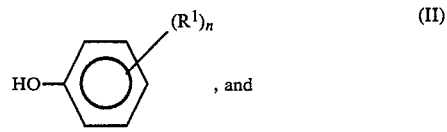

, and

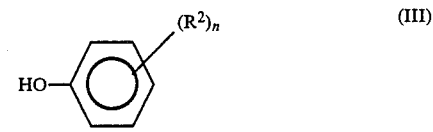

with a difunctional agent selected from the group consisting of:

a vicinal glycol of the formula (IV)

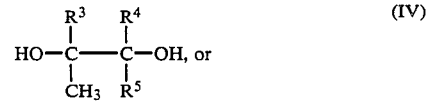

an unsaturated alcohol of the formulae (VA), (VB), or (VC)

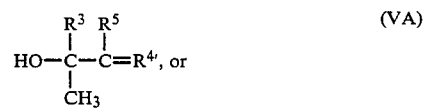

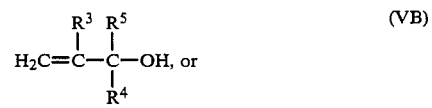

-continued

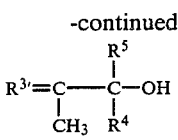 (VC)

a diene selected from the formulae (VI and VII)

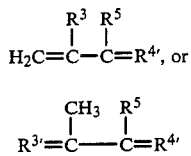 (VI)

(VII)

wherein the divalent hydrocarbon radicals represented by $R^{3'}$ and $R^{4'}$ are lower alkylidene, aralkylidene and cycloalkylidene radicals,
to form a bisphenol of formula (I).

2. The process for the preparation of a bisphenol as set forth in claim 1, wherein said phenol is

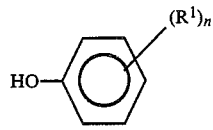

3. The process for the preparation of a bisphenol as set forth in claim 1, wherein said phenol is

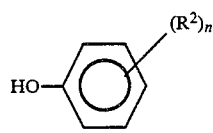

4. The process for the preparation of a bisphenol as set forth in claim 1, wherein said difunctional agent is a vicinal glycol of the formula (IV).

5. The process for the preparation of a bisphenol as set forth in claim 4, wherein said vicinal glycol is selected from the group consisting of 2,3-dimethyl-2,3-butanediol, 2,3-dimethyl-2,3-pentanediol, 2,3-dimethyl-2,3-hexanediol, 2,3-diphenyl-2,3-butanediol, 2-methyl-3-phenyl-2,3-butanediol, 2-methyl-3-ethyl-2,3-hexanediol, 2-methyl-2,3-butanediol, 3-methyl-2,3-pentanediol, and 2,3-di(p-tolyl)-2,3-butanediol.

6. The process for the preparation of a bisphenol as set forth in claim 1, wherein said difunctional agent is unsaturated alcohol of the formula (VA).

7. The process for the preparation of a bisphenol as set forth in claim 1, wherein said difunctional agent is an unsaturated alcohol of the formula (VB).

8. The process for the preparation of a bisphenol as set forth in claim 1, wherein said difunctional agent is an unsaturated alcohol of the formula (VC).

9. The process for the preparation of a bisphenol as set forth in claim 1, wherein said difunctional agent is an unsaturated alcohol selected from the group consisting of 2-hydroxy-2-methyl-3-butene 2,3-dimethyl-3-hydroxy-1-pentene, 2-hydroxy-3-methyl-2-phenyl-3-butene, and 3-hydroxy-2,3,4-trimethyl-4-pentene.

10. The process for the preparation of a bisphenol as set forth in claim 1, wherein said difunctional agent is a diene of the formula (VI).

11. The process for the preparation of a bisphenol as set forth in claim 1, wherein said difunctional agent is a diene of the formula (VII).

12. The process for the preparation of a bisphenol as set forth in claim 1, wherein said difunctional agent is a diene selected from the group consisting of 2,3-dimethyl-1,3-butadiene, isoprene, 2,3-dimethyl-1,3-pentadiene, 2-metehyl-3-phenyl-1,3-butadiene, 2-methyl-1,3-hexadiene, and 2-phenyl-1,3-pentadiene.

13. The process for the preparation of a bisphenol as set forth in claim 1, wherein at least one of $R^1$ and $R^2$ is chlorine or bromine.

14. The process for the preparation of a bisphenol as set forth in claim 1, wherein at least one of $R^1$ and $R^2$ is a monovalent hydrocarbon radical of one to four carbon atoms.

15. The process for the preparation of a bisphenol as set forth in claim 1, wherein at least one of $R^1$ and $R^2$ is a monovalent alkoxy radical of one to six carbon atoms.

16. The process for the preparation of a bisphenol as set forth in claim 1, wherein $R^5$ is hydrogen.

17. The process for the preparation of a bisphenol as set forth in claim 1, wherein at least one of $R^3$, $R^4$, and $R^5$ is selected from the group consisting of alkyl radicals of 1 to 8 carbon atoms, and cycloalkyl radicals of 4 to 8 carbon atoms.

18. The process for the preparation of a bisphenol as set forth in claim 1, wherein at least one of $R^3$, $R^4$, and $R^5$ is an aryl radical of 6 to 12 carbon atoms.

19. The process for the preparation of a bisphenol as set forth in claim 1, wherein at least one of $R^3$, $R^4$, and $R^5$, is selected from the group copnsisting of alkaryl radicals of 7 to 14 carbon atoms, and aralkyl radicals of 7 to 14 carbon atoms.

20. The process for the preparation of a bisphenol of formula (I) as set forth in claim 1, wherein $R_3$, $R_4$, and $R_5$ are independently selected from a lower alkyl radical of one to four carbon atoms, an aryl radical of six to twelve carbon atoms, an alkaryl radical of seven to fourteen carbon atoms, an aralkyl radical of seven to fourteen carbon atoms, and a cycloalkyl radical of four to eight carbon atoms; and $R_5$ may also be hydrogen.

21. The process for the preparation of a bisphenol as set forth in claim 1, wherein at least one of $R_3$, $R_4$, and $R_5$ is an alkyl radical of one to six carbon atoms.

* * * * *